United States Patent [19]
Kita

[11] Patent Number: 5,303,021
[45] Date of Patent: Apr. 12, 1994

[54] OPTICAL DETECTOR FOR CAPILLARY CHROMATOGRAPHY

[75] Inventor: Jun-ichi Kita, Kyoto, Japan

[73] Assignee: Shimadzu Corporation, Kyoto, Japan

[21] Appl. No.: 810,873

[22] Filed: Dec. 20, 1991

[30] Foreign Application Priority Data

Dec. 28, 1990 [JP] Japan .................................. 2-416041

[51] Int. Cl.[5] ...................... G01N 21/85; G01N 30/74
[52] U.S. Cl. ...................................... 356/72; 356/246; 356/410
[58] Field of Search ................ 356/72, 246, 410, 440, 356/429, 326, 328

[56] References Cited

U.S. PATENT DOCUMENTS

| | | | |
|---|---|---|---|
| 3,655,980 | 4/1972 | Bossen | 356/429 X |
| 4,172,227 | 10/1979 | Tyrer et al. | 356/417 X |
| 4,375,163 | 3/1983 | Yang | 356/72 |
| 4,576,477 | 3/1986 | Corbet et al. | 356/442 X |
| 4,618,769 | 10/1986 | Johnson et al. | 356/246 |
| 4,747,686 | 5/1988 | Sato | 356/72 |

Primary Examiner—Vincent P. McGraw
Attorney, Agent, or Firm—William L. Klima

[57] ABSTRACT

In order to improve a signal-to-noise ratio of an optical detector with a light source and a photodetector of ordinary performance, light is applied from an ultraviolet lamp 6 which is provided on one side of a capillary cell 4 while light generated from the capillary cell 4 is received by an array photodetector 14 provided on the other side thereof. A lens 18 makes positions on the capillary cell 4 to correspond to those on the array photodetector 14. A data processing part 20 temporarily stores corrected and incorporated detection outputs, and calculates integrated averages while displacing time bases so that those of the same sample portions are overlapped with each other.

6 Claims, 5 Drawing Sheets

OPTICAL DETECTOR FOR CAPILLARY CHROMATOGRAPHY

BACKGROUND OF THE INVENTION

1. Field of the Invention

The present invention relates to an optical detector which is employed for an analyzer utilizing a capillary chromatography, and more particularly, it relates to an optical detector which is applied to a capillary electrophoresis apparatus, a liquid chromatography apparatus, or the like.

2. Description of the Background Art

It is preferable that the limit of detection of an analyzer, i.e., the signal-to-noise ratio of a detector, is as high as possible. In an optical detector, luminance of a light source is limited while samples or a capillary are deteriorated when light of excessive intensity is employed. Further, sensitivity of the detector also has a certain limit due to its detection principle.

When detection is performed in a photon count region in order to improve sensitivity, it takes so much time that no dynamic range can be obtained.

Thus, the signal-to-noise ratio of a detection system is inevitably limited even if the same is formed by an optimum light source, an optimum optical system and an optimum detector.

SUMMARY OF THE INVENTION

An object of the present invention is to provide an optical detector for a capillary chromatography, which can improve the signal-to-noise ratio with a light source and a photodetector of ordinary performance.

In a signal detecting portion of a capillary, the original signal waveform is hardly changed even if a detecting position is slightly displaced. According to the present invention, therefore, an optical system is so arranged as to guide signals received from some points of a signal detecting portion of a capillary to a plurality of photodetecting elements, signals of the same waveform, which are outputted from each photodetecting element with slight time lags, are overlapped by computing the time lags and an average value of each spectrum is evaluated, thereby the signal-to-noise ratio of the overall system of measurement is improved.

Referring to FIGS. 1 and 2 showing an embodiment of the present invention, the inventive optical detector for a capillary chromatography comprises a capillary cell 4 of a prescribed length which is supplied with a flow of a sample solution, a light application part 12 for converging light which is emitted from a light source 6 onto the capillary cell 4, an array photodetector 14 which is provided with a plurality of photodetecting elements, an optical system 18 for guiding signal light received from the capillary cell 4 onto the array photodetector 14 so that positions of the capillary cell 4 correspond to the photodetecting elements which are provided on the array photodetector 14, and a data processing part 20 for incorporating outputs from the photodetecting elements of the array photodetector 14 and data-processing the same. The data processing part 20 comprises a storage part 24 for storing the outputs from the photodetecting elements, and an integrated average operating part 26 for calculating integrated average values of outputs for the same sample portions as to the outputs of the photodetecting elements stored in the storage part 24.

In order to correct differences in sensitivity, which may be caused between the photodetecting elements of the array photodetector 14 including aberration of the optical system 18, a correction part 22 having a correction coefficient is further provided for correcting the outputs from the photodetecting elements with the correction coefficient.

FIG. 3 shows exemplary time-base waveforms of detection outputs $Vf(n)$ and $Vf(n+1)$ of n-th and (n+1)th photodetecting elements of the array photodetector 14. Namely, the waveforms of the detection outputs $Vf(n)$ and $Vf(n+1)$ are displaced by a time $\Delta t$ from each other. These data are temporarily stored in the storage part 24, for calculation of an integrated average of the output $Vf(n)$ and that displaced from the output $Vf(n+1)$ by the time $\Delta t$. Such integrated averages are calculated for all photodetecting elements of the array photodetector 14.

The time lag $\Delta t$ between each adjacent pair of the photodetecting elements may be evaluated by two methods. In the first method, a sample which can provide a single peak is measured and a time lag $\Delta t$ in the analyzing condition therefor is obtained from displacement of peak positions, as shown in FIG. 4.

In the second method, the time lag $\Delta t$ is obtained from a signal peak of a sample for measurement itself.

When integrated averages are calculated, noise is reduced at the inverse square root of a number N of times of integration, for the following reason: Assuming that $Vi$ represents an output of an i-th photodetecting element at a certain time, an equation $Vi = Vm + Vni$ can be set, where $Vm$ represents an average value of $Vi$, and $Vni$ represents a noise component of $Vi$. An integrated average is calculated as follows:

$$\frac{\sqrt{\left(\sum_{i=1}^{N} Vi\right)^2}}{N} = Vm + \frac{Vni}{\sqrt{N}}$$

A method of correcting differences in sensitivity between the photodetecting elements is now described.

A large quantity of a fluorescent material is injected into the capillary in the case of fluorescence detection, while a large quantity of a UV absorbent material is injected therein in the case of UV absorbent detection, so that a portion for receiving signal light with a plurality of photodetecting elements is entirely filled up with the material. When outputs of all photodetecting elements are obtained in this state, the outputs differ from each other due to dispersion in sensitivity between the photodetecting elements or aberration of the optical system, although the outputs must be originally at the same signal voltage (amount of charges).

Since the amounts of signals received in the photodetecting elements are proportionate to output charges, it is conceivable that the differences in sensitivity between the photodetecting elements are merely related to proportion coefficients.

Further, since the axis of ordinates of a chromatogram is at an arbitrary scale, a correction coefficient $Fn$ for an n-th photodetecting element can be obtained as $Fn = Vol/Von$ with reference to a first photodetecting element, assuming that $Vol$ represents the output of the first photodetecting element and $Von$ represents that of the n-th photodetecting element. This correction coefficient is stored in a memory device, so that a corrected output Vfn is obtained as Vfn=Von.Fn in actual measurement by multiplying the output of each photodetecting element by this correction coefficient.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
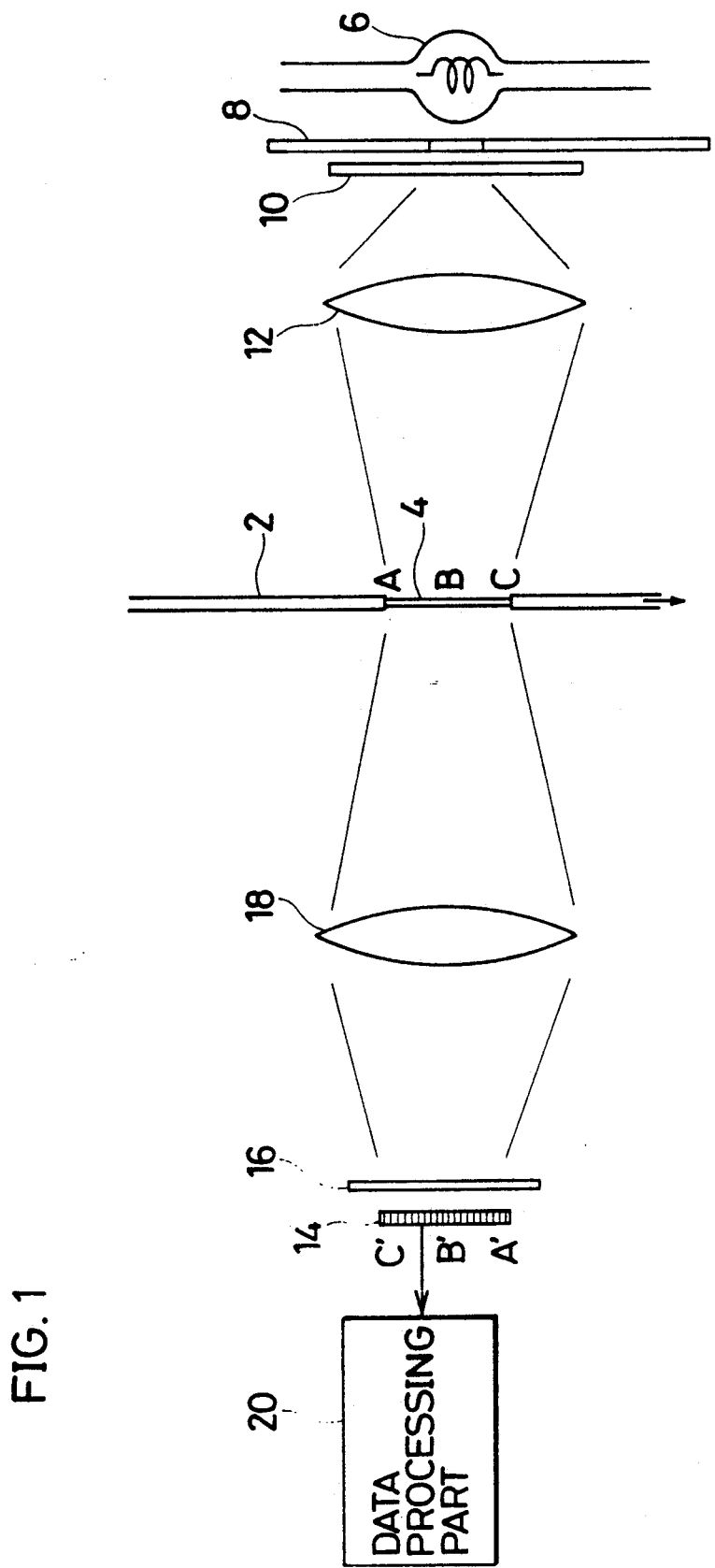
FIG. 1 is a schematic block diagram showing an embodiment of the present invention.

FIG. 1 shows an embodiment of the present invention, which is applied to a detector for a capillary electrophoresis apparatus.

A coating material of a capillary 2 is removed from an optical detector portion over a constant length, to define a capillary cell 4. A material, such as DNA, for example, which is labelled with a fluorescent material flows in the capillary 2. It is assumed that this labelling fluorescent material emits fluorescence of about 600 nm.

An ultraviolet lamp 6 is arranged on one side of the capillary cell 4 for serving as a light source, while an aperture 8 for limiting light emitted from the ultraviolet lamp 6, an optical filter 10 for converting the light to a beam having a central wavelength of 300 nm, and a lens 12 for converging the light which is passed through the optical filter 10 onto the capillary cell 4 are provided between the ultraviolet lamp 6 and the capillary cell 4.

A one-dimensional array photodetector 14 is arranged on the other side of the capillary cell 4, while a lens 18 for converging light which is generated from the capillary cell 4 onto the one-dimensional array photodetector 14 and an optical filter 16 having a central wavelength of 600 nm for passing fluorescence of about 600 nm which is generated from the capillary cell 4 and intercepting excitation light are arranged between the capillary cell 4 and the one-dimensional array photodetector 14.

Fluorescence components which are generated at positions A, B and C on the capillary cell 4 form images on positions A', B' and C' of the one-dimensional array photodetector 14 respectively.

The one-dimensional array photodetector 14 performs sampling from the respective photodetecting elements at sampling rates higher than 50 milliseconds (20 Hz).

A data processing part 20 incorporates detection outputs of the respective photodetecting elements from the one-dimensional array photodetector 14, to correct differences in sensitivity between the photodetecting elements and obtain integrated averages.

Figure 2:
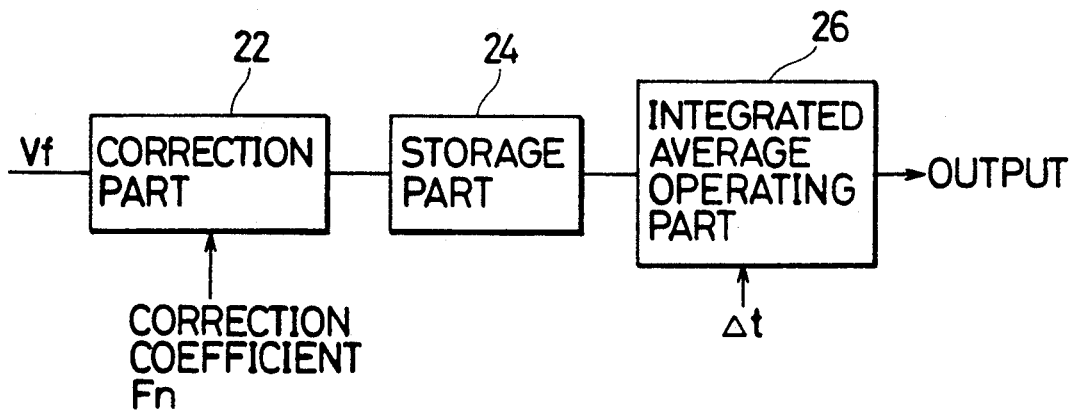
FIG. 2 is a block diagram showing the function of a data processing part.

As shown in FIG. 2, the data processing part 20 comprises a correction part 22 for correcting the differences in sensitivity, a storage part 24 for temporarily storing the corrected and incorporated detection outputs, and an integrated average operating part 26 for calculating integrated averages.

The operation of this embodiment is now described.

Figure 5:
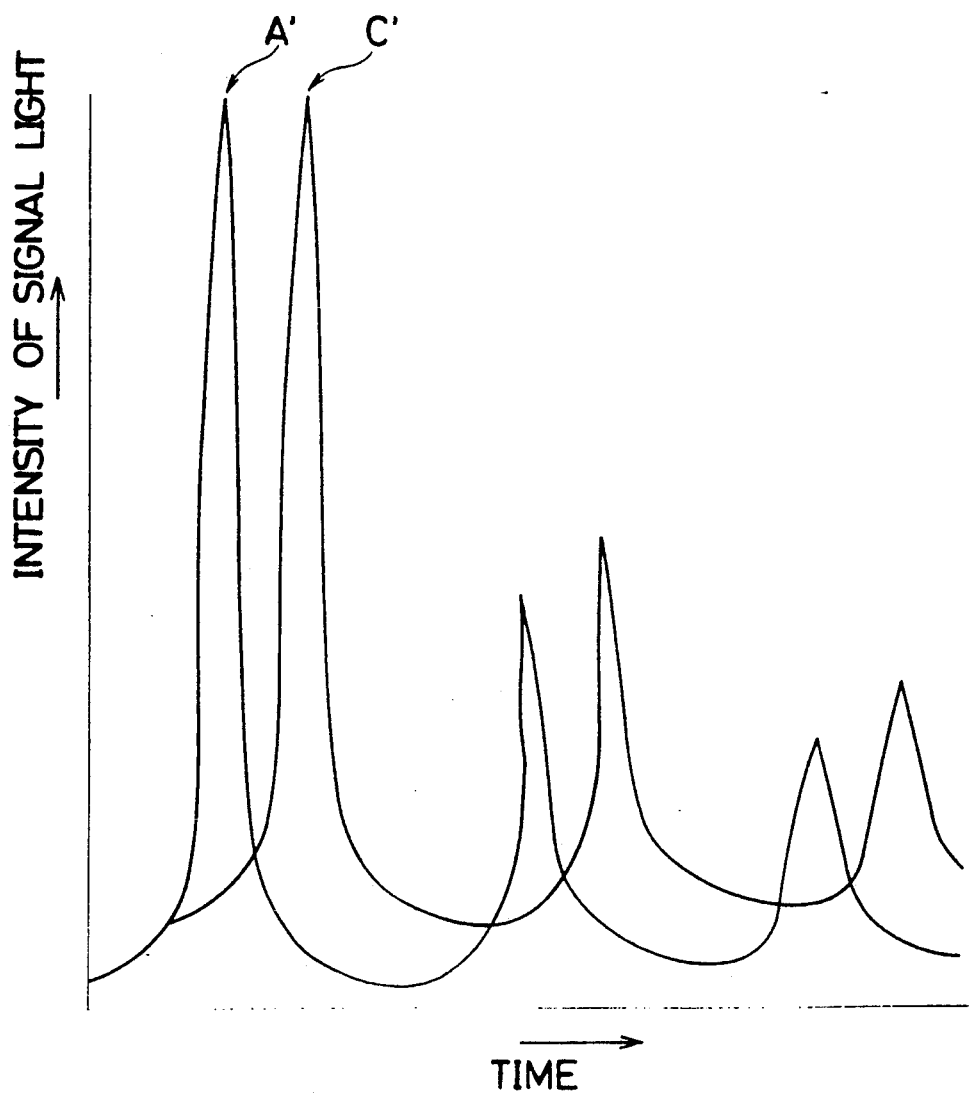
FIG. 5 illustrates exemplary photodetecting element outputs.
Figure 3:
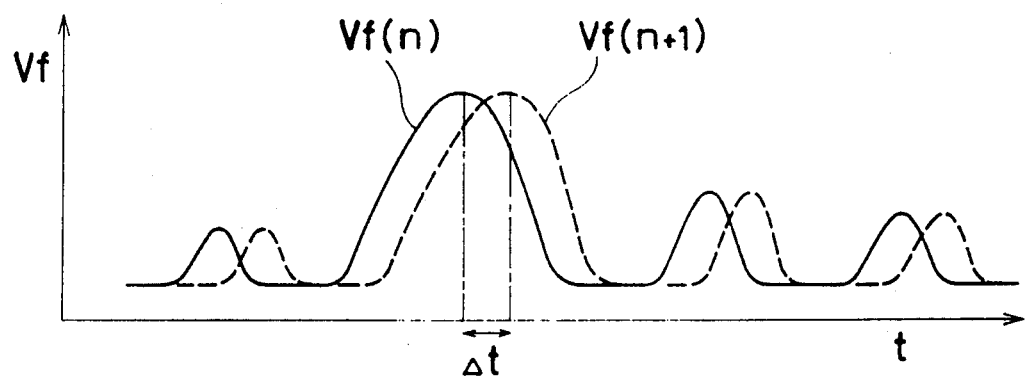
FIG. 3 illustrates detection signal waveforms of adjacent photodetecting elements.
Figure 4:
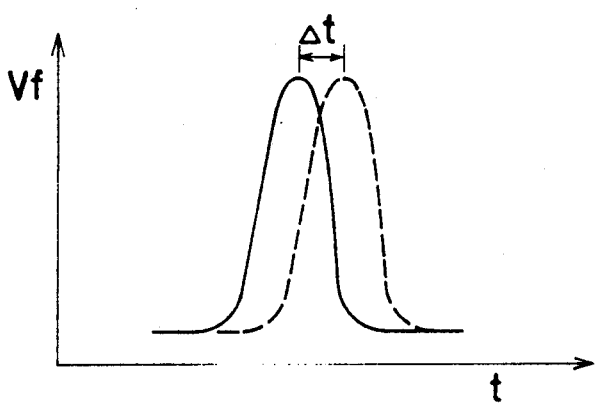
FIG. 4 illustrates waveforms of adjacent detecting elements detected upon measurement of a sample which provides a single peak.

Since the length of a part of the capillary cell 4, which generates the signal light components to be received by the respective photodetecting elements of the one-dimensional array photodetector 14, is extremely short as compared with the overall length of the capillary cell 4, a waveform profile obtained in the photodetecting element at the position A' of the one-dimensional array photodetector 14 hardly differs from that obtained in the photodetecting element at the position C', while the two have a difference in time to become spectra having a time lag as shown in FIG. 5. Although FIG. 5 shows only signal light outputs from the photodetecting elements at the positions A' and C', such spectra are obtained from all photodetecting elements of the one-dimensional array photodetector 14 in practice.

Figure 6:
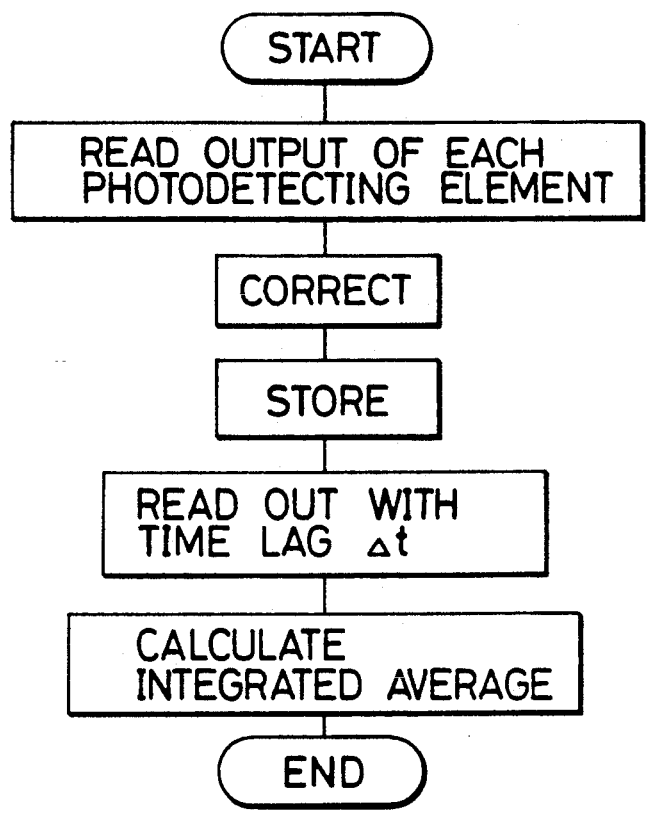
FIG. 6 is a flow chart showing the operation of the embodiment.

FIG. 6 shows steps of data processing. The outputs from the respective photodetecting elements of the one-dimensional array photodetector are read, corrected and then stored in a memory device. The as-stored spectra of the respective photodetecting elements are read out with time lags, for calculation of integrated averages. Due to the integrated averages, the signal-to-noise ratio is improved in reverse proportion to the square root of the number of the photodetecting elements, as compared with a spectrum from a single detecting element.

Although the aforementioned embodiment is applied to a single capillary, the present invention is also applicable to a plurality of capillaries.

Figure 7:
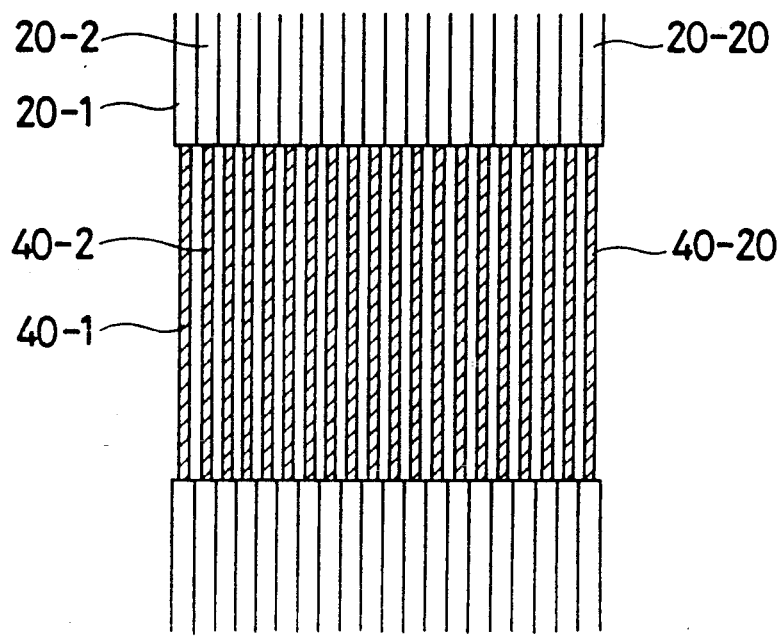
FIG. 7 is a front elevational view showing a capillary cell part of another embodiment of the present invention, which employs a plurality of capillaries.

Referring to FIG. 7, 20 capillaries 20-1 to 20-20 of 75 μm in inner diameter, for example, are arranged on a plane in a bundle. Coating materials are removed from portions for defining capillary cells 40-1 to 40-20 over a prescribed length. Such capillaries 20-1 to 20-20 are arranged in place of the capillary 2 shown in FIG. 1 perpendicularly to an optical axis, while a two-dimensional array photodetector such as a CCD is substituted for the one-dimensional array photodetector 14 shown in FIG. 1, to simultaneously receive signal light components from the capillary cells 40-1 to 40-20. Other structure is identical to that of FIG. 1.

According to the structure shown in FIG. 7, it is possible to measure a plurality of capillaries with an excellent signal-to-noise ratio.

The photodetector is not restricted to an array photodetector such as a CCD, but the same may alternatively be formed by a device such as an image pickup tube, for example, so far as the same is sensitive to signal light.

Figure 8:
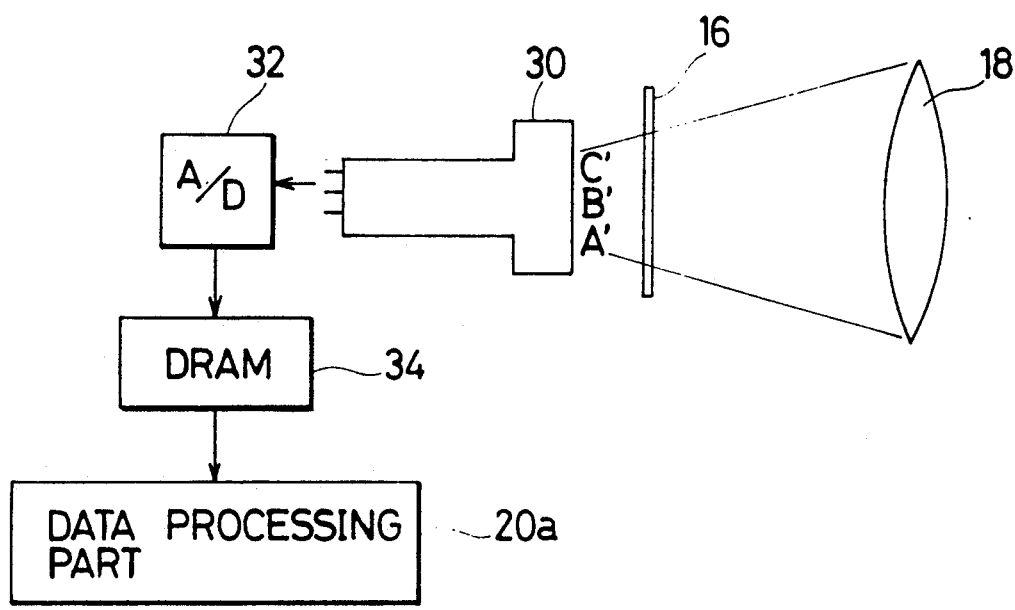
FIG. 8 shows still another embodiment of the present invention, which employs an image pick-up tube as a photodetector.

FIG. 8 shows still another embodiment of the present invention, which employs an image pick-up tube as a photodetector.

A sample solution flowing in a capillary cell is excited by the same optical system as that shown in FIG. 1, so that the as-generated fluorescence is converged by a lens 18 to form an image on an image pick-up plane of an image pick-up tube 30 through an optical filter 16. A luminance image formed by the image pick-up tube 30 is converted to a digital signal by an A-D converter 32, and temporarily stored in a DRAM (Dynamic Random Access Memory) 34. The DRAM 34 stores not all pixel data provided on the image pick-up plane, but only data on lines corresponding to the image of the capillary cell. The data stored in the DRAM 34 are processed by a data processing part 20a, similarly to the embodiment shown in FIG. 1.

The DRAM 34 may be replaced by SRAM (Static RAM).

The single image pick-up tube 30 can also cope with the plurality of capillary cells shown in FIG. 7.

According to the present invention, signal light which is emitted from a sample flowing in a capillary cell is received by a plurality of photodetecting elements for obtaining integrated averages of outputs having time lags from the plurality of photodetecting elements as to the same sample, whereby it is possible to perform measurement in a higher signal-to-noise ratio as compared with a conventional method.

Further, it is possible to perform measurement in a much higher signal-to-noise ratio by correcting differences in sensitivity between the photodetecting elements.

Although the present invention has been described and illustrated in detail, it is clearly understood that the same is by way of illustration and example only and is not to be taken by way of limitation, the spirit and scope of the present invention being limited only by the terms of the appended claims.

I claim:

1. An optical detector for a capillary chromatography, comprising:
    a capillary supplied with a flow of a sample solution;
    a capillary cell defined by a portion of said capillary;
    a light application part for converging light from a light source onto said capillary cell;
    an array photodetector provided with a plurality of photodetecting elements aligned with a direction of flow through the capillary cell;
    an optical system for guiding signal light from said capillary cell onto said array photodetector so that positions of said capillary cell correspond to said photodetecting elements on said array photodetector; and
    a data processing part for incorporating outputs from said photodetecting elements of said array photodetector and data-processing the outputs, said data processing part provided with a storage part for storing said outputs from said photodetecting elements and an integrated average operating part for calculating integrated averages of outputs from the same sample portions detected by different photodetecting elements with differences in time as to said outputs from said photodetecting elements stored in said storage part.

2. An optical detector in accordance with claim 1, wherein a plurality of said capillary cells are arranged in parallel with each other on a plane being perpendicular to an optical axis, and said array photodetector is formed by a two-dimensional array photodetector for simultaneously receiving signal light components from said plurality of capillary cells.

3. An optical detector in accordance with claim 1, further comprising a correction part having a correction coefficient for correcting differences in sensitivity between said photodetecting elements of said array photodetector for correcting outputs from respective said photodetecting elements with said correction coefficient.

4. An optical detector for a capillary chromatography, comprising:
    a capillary supplied with a flow of a sample solution;
    a capillary cell defined by a portion of said capillary;
    a light application part for converging light from a light source onto said capillary cell;
    an image pick-up tube;
    an optical system for guiding signal light from said capillary cell onto said image pick-up tube so that positions of said capillary cell correspond to photodetecting positions on said image pick-up tube; and
    a data processing part for incorporating outputs from said image pick-up tube and data-processing the outputs, said data processing part provided with a storage part for storing outputs of said photodetecting positions of said image pick-up tube and an integrated average operating part for calculating integrated averages of outputs from the sample portions detected by difference photodetecting positions with differences in time as to said outputs of said photodetecting positions stored in said storage part.

5. An optical detector in accordance with claim 4, wherein a plurality of said capillary cells are arranged in parallel with each other on a plane being perpendicular to an optical axis.

6. An optical detector in accordance with claim 4, further comprising a correction part having a correction coefficient for correcting differences in sensitivity between said photodetecting positions of said image pick-up tube for correcting outputs from respective said photodetecting positions with said correction coefficient.

* * * * *